United States Patent [19]

Shukunobe et al.

[11] Patent Number: 4,965,051
[45] Date of Patent: Oct. 23, 1990

[54] REACTOR PROVIDED WITH FLUIDIZED CHAMBER

[75] Inventors: Yukitaka Shukunobe, Kawagoe; Tetsuo Nakamura, Iruma; Tomoe Yoshida, Tokorozawa; Ryoichi Doki, Sayama; Mamoru Kuwazuru, Kawagoe; Kouzou Shimoda, Tokyo, all of Japan

[73] Assignee: R&D Association for Bioreactor System, Tokyo, Japan

[21] Appl. No.: 319,246

[22] Filed: Mar. 6, 1989

[30] Foreign Application Priority Data

Mar. 9, 1988 [JP] Japan .................................. 63-55756

[51] Int. Cl.$^5$ .............................. B01J 8/02; B01J 8/20
[52] U.S. Cl. .................................... 422/145; 422/219; 422/233; 422/292; 134/166; 134/177; 250/431
[58] Field of Search ............... 422/219, 232, 233, 140, 422/143, 145, 292, 24; 134/25.1, 166 R, 169 R, 177, 186; 250/431, 432 R, 433, 434, 435

[56] References Cited

U.S. PATENT DOCUMENTS 3,923,663 12/1975 Reid .................................. 422/24 X
4,670,140 6/1987 Aivasidis et al. ............... 422/193 X

FOREIGN PATENT DOCUMENTS

61-12280 1/1986 Japan .

Primary Examiner—Robert J. Warden
Assistant Examiner—Jeffrey R. Snay
Attorney, Agent, or Firm—Griffin, Branigan & Butler

[57] ABSTRACT

The present invention relates to a method of disinfecting immobilized biocatalysts in which the extinguishing of microbes adhering to carriers without lowering the activity of immobilized biocatalysts by irradiating ultraviolet light to immobilized biocatalysts at the illuminating power of less than 0.5mW/cm$^2$, and to a reactor provided with fluidized chamber wherein a column chamber with outflow-preventing net is connected with an end of fluidized chamber, and an inner tube with an outflow-preventing net at the head opening and at the same time movable in the fluidized chamber is connected with a column chamber, and at the other side of the fluidized chamber a washing gateway with an outflow-preventing net is connected so as to be able to be washing, disinfecting, adsorbing and eluting of reaction continuously.

3 Claims, 5 Drawing Sheets

REACTOR PROVIDED WITH FLUIDIZED CHAMBER

BACKGROUND OF THE INVENTION

The present invention relates to a method of and apparatus for washing and disinfecting immobilized enzymes or immobilized myceliums (hereinafter referred to as immobilized biocatalysts). In one aspect of the invention, disinfecting is achieved by using irradiation of ultraviolet light and, in another aspect, the apparatus reduces the difficulties of washing and disinfecting immobilized biocatalysts and provides for adsorption of useful materials to a gel, an immobilized carrier or the like. The reactor may use a raw material, including materials to which protein or the like is easily attached, the reactor is provided with a fluidized chamber which can wash and disinfect without disactivating immobilized biocatalysts.

Heretofore, the art of production using immobilized biocatalysts has been extremely innovative and there are many reactors such as the packed layer type, the fluidized bed type, the stirred tank type and the membrane type used in this field.

In regard to the art of washing and disinfecting of the present invention, there is background art disclosed in the Japanese Patent Publication No. 33873/87, using surface active agent like quaternary ammonium salt, or propylene glycol in 10–50% or the like as disinfectant.

As for the method of disinfection in said Japanese Patent Publication No. 33873/87, a lowering of activity of immobilized enzymes is inevitable, and if any measures against the lowering thereof are taken, then there is a dilemma in that the effect of disinfection is decreased.

Further, in regard to the art concerning reactor provided with fluidized chamber in the present invention, there is disclosed in Japanese Patent Publication No. 33873/87, the art of washing and disinfecting immobilized biocatalysts in reactors, which are separate from but connected to an apparatus for washing and disinfecting immobilized biocatalysts in a closed circuit to enable cycling of immobilized biocatalysts dispersed in water. But on account of the said reactor and an apparatus for washing and disinfecting immobilized biocatalysts being separate, there are various problems, such as the need for a separate space for the apparatus for washing and disinfecting, resulting in an uneconomical increase of cost.

Therefore, there is another disclosure by the present inventor in Japanese Patent Provisional Publication No. 336364/87 corresponding to U.S. patent application Ser. No. 07/278,306. In this prior application, when the washing and disinfecting of immobilized biocatalysts is conducted, an inner tube is taken up so as to bring an outer a head opening into contact with an inner surface of an upper surface of funnel a portion of a fluidized chamber. Then washing liquid is introduced into the reactor at high pressure through the lower portion of a column chamber connected to the fluidized chamber, and by a vortex flow of the washing liquid being generated mainly in the fluidized chamber, the washing and stirring of immobilized biocatalysts and washing of column chamber and apparatus in the fluidized chamber is operated at the same time.

However, as for the reactor provided with fluidized chamber of Japanese Patent Provisional Publication No. 336364/87, because of the washing and stirring of immobilized biocatalysts and washing of the column chamber and apparatus being operated at the same time, as above stated, it results in the lowering of activity of immobilized biocatalysts when washing mainly for the purpose of washing the column chamber and the fluidized chamber similarly, when washing mainly for the purpose of washing immobilized biocatalysts, then the washing of the column chamber and the fluidized chamber is not operated sufficiently for effective washing.

Further, in the said prior application, disinfection is made by using surface active agent like quaternary ammonium salt after washing immobilized biocatalysts, but the effect of disinfection is insufficient.

SUMMARY OF THE INVENTION

Accordingly, the present invention provides a method of disinfecting immobilized biocatalysts without lowering the activity of immobilized biocatalysts which has an effect of disinfection at the same time.

According to the present invention, there is provided a method of an apparatus for disinfecting of immobilized biocatalysts by using the irradiation of ultraviolet light to immobilized biocatalysts at an illuminating power of less than 0.5 mW/cm$^2$ so as to destroy microbes adhering to the carriers of the biocatalysts without lowering the activity of immobilized biocatalysts.

In addition, the present invention provides a reactor provided with fluidized chamber which can wash immobilized biocatalysts, the column chamber and apparatus in the fluidized chamber simultaneously, and further, can wash the column chamber and apparatus in a fluidized chamber sufficiently without lowering the activity of immobilized biocatalysts on account of the washing.

According to the present invention, there is also provided a reactor provided with fluidized chamber characterized in that a fluidized chamber is connected at one end with a column chamber having a net or screen for preventing the outflow of solids and a lower net or screen for preventing the outflow of solids. The column chamber is contacted with an inner tube having a net or screen for preventing the outflow of solids at its head opening and at the same time arranged to be movable in the fluidized chamber. The fluidized chamber is connected at another end with a net or screen for preventing the outflow of solids, and a gateway for introducing washing liquid or the like and having a net or screen for preventing the outflow, of solids so that the process of washing, disinfecting, adsorbing and reacted eluting is operated continuously.

The present invention has the following advantages:

In the method of disinfecting immobilized biocatalysts, by using the irradiation of ultraviolet light to immobilized biocatalysts at illuminating power of less than 0.5 mW/cm$^2$, the disinfecting effect is considerably more developed than the conventional disinfectants, and therefore it enables one to prevent the lowering of activity of immobilized biocatalysts. And as for the method of irradiating, both overhead irradiation and dipping irradiation are available provided that the ceiling value of the irradiation of ultraviolet light is set at illuminating power of less than 0.5 mW/cm$^2$.

Further, in the reactor provided with fluidized chamber the washing of immobilized biocatalysts and the washing of a column chamber and apparatus in a fluidized chamber are operated simultaneously, moreover, separately.

BRIEF DESCRIPTION OF THE DRAWINGS

The above and other advantages of the invention will be apparent from the reference to the description taken in connection with the accompanying drawings, in which.

DESCRIPTION OF THE INVENTION

In regard to the experimental examples of the method of disinfection by using ultraviolet light in the present invention the following are shown:

EXAMPLE 1

There made a comparison between the method of irradiating ultraviolet light from the overhead of immobilized biocatalysts solution to the said immobilized biocatalysts solution by using an ultraviolet lamp (hereinafter referred to as overhead irradiation) and the method of dipping the ultraviolet lamp into the said immobilized biocatalysts solution (hereinafter referred to as dipping irradiation). In the experient protease "S" was used as immobilized enzymes and "chitopearl" (trademark) was used as carriers, and illuminating power of irradiation of the ultraviolet light was set at $0.5 \ mW/cm^2$ on the surface of solution by overhead irradiation, and at $4.4 \ mW/cm^2$ at 1.9 cm from the illuminant by dipping irradiation.

Figure 3:
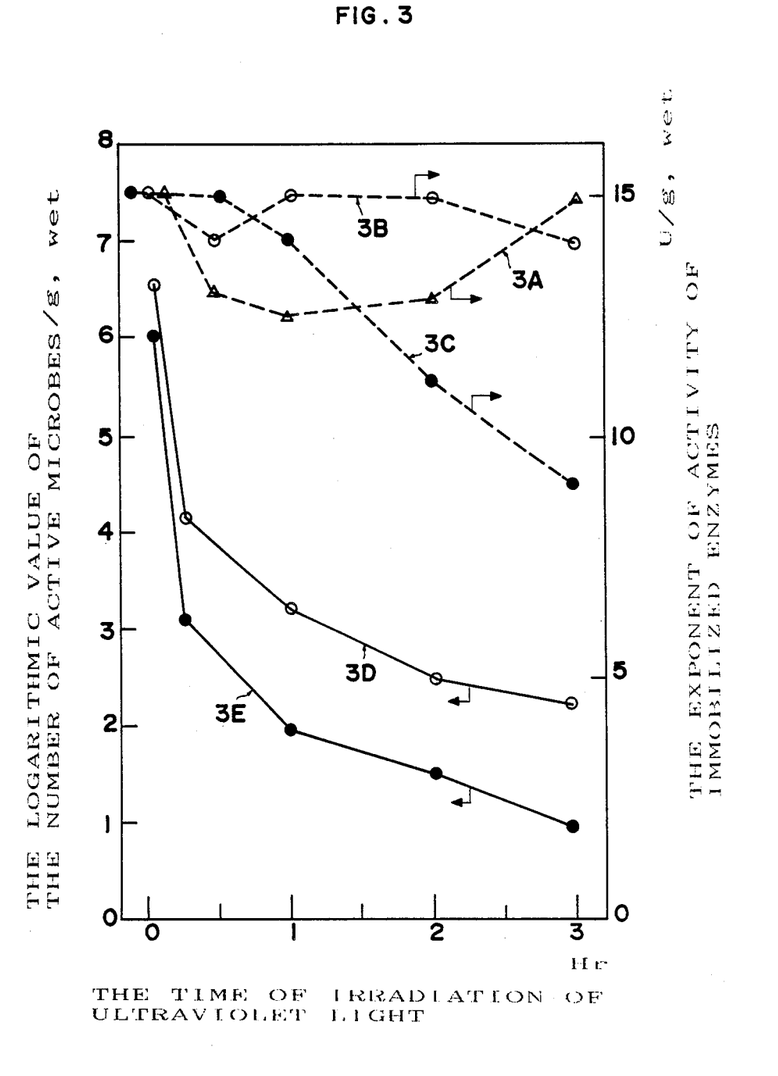
FIG. 3, more specifically, is a graphic chart showing effect of disinfection and activity of immobilized biocatalysts as for overhead irradiation and dipping irradiation by using ultraviolet light, FIG. 4, more specifically, is a graphic chart showing the results of irradiating experiment varying the illuminating power of irradiation of ultraviolet light as for the overhead irradiation of FIG. 3, and FIG. 5, more specifically, is a graphic chart showing the decreasing of the number of active microbes by disinfection using overhead irradiation and dipping irradiation of ultraviolet light at the illuminating power of $0.5 \ mW/cm^2$.

The above experiment resulted in the graphic chart shown as in FIG. 3. Further, dotted lines 3A, 3B and 3C in FIG. 3 are indicated as the time of irradiation of ultraviolet light for the horizontal axis and as the exponent of activity of immobilized enzymes for the vertical axis, and solid lines 3D, 3E are expressed as the time of irradiation of ultraviolet light for the horizontal axis and the logarithmic value of the number of active microbes for the vertical axis. And as for the conditions of irradiations of ultraviolet light, 3A was made with no irradiation of ultraviolet light so that it shows the temporal fluctuation of activity of immobilized enzymes graphically. 3B and 3D show the results by overhead irradiations of $0.5 \ mW/cm^2$ on the surface of solution, and 3C and 3E show the results by dipping irradiations of $4.4 \ mW/cm^2$ at 1.9 cm from the illuminant.

In the above experiment there is proved that the longer the irradiating time is, the more effective the effect of disinfection becomes by using ultraviolet light because the effect of disinfection is propotional to the product of illuminance of effective irradiation and time of irradiation.

And in regard to the effect of disinfection, the number of active microbes of immobilized enzymes were firstly at the order of $10^6$ per 1 g.wet of immobilized enzymes, and after two hours of overhead irradiation, the number became at the order of $10^2$. On the other hand dipping irradiation produced a lower value of the number of active microbes of immobilized enzymes at one order than using overhead irradiation and therefore the disinfecting effect was accordingly.

While in regard to the activity of immobilized enzymes, there were no lowering of activity by using overhead irradiation, and on the other hand by using dipping irradiation the activity became lower after one hour of irradiation, and then it declined to almost half after three hours from the beginning of irradiation.

EXAMPLE 2

Figure 4:
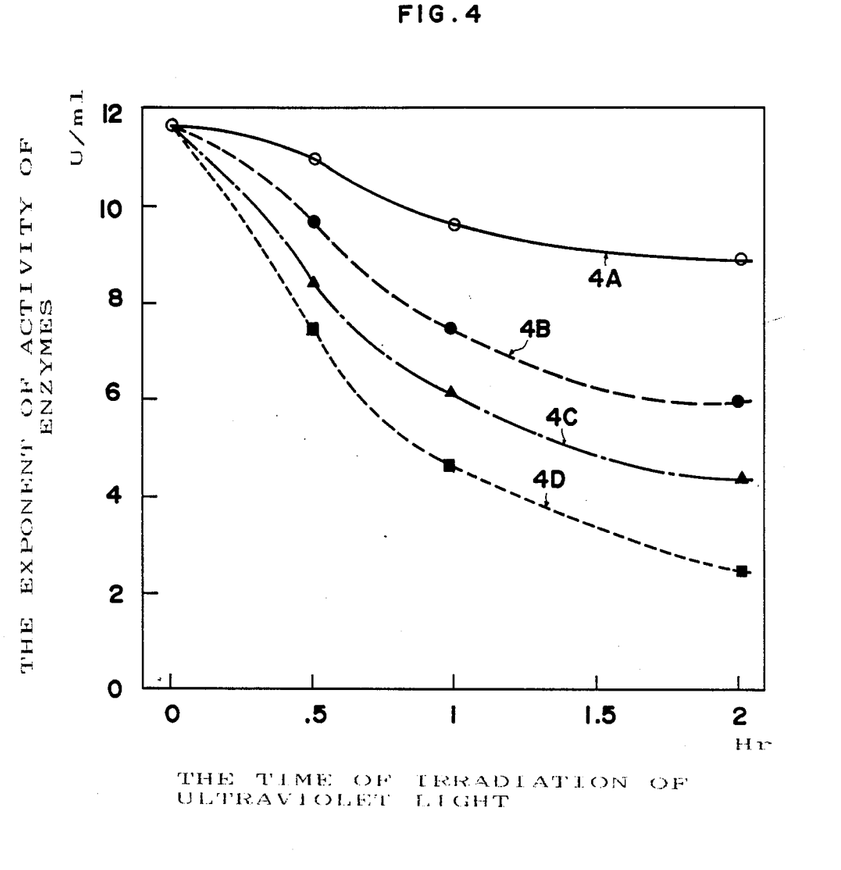

Supposing that the reason of the lowering of activity of immobilized enzymes by dipping irradiation mentioned above is owing to the illuminating power of ultraviolet light, another result was acquired as shown in FIG. 4, in which the experiment of overhead irradiation to soluble enzymes solution was made by varying the illuminating power of ultraviolet light. In FIG. 4, the horizontal axis indicates the time of irradiation of ultraviolet light, and the vertical axis indicates the exponent of activity of enzymes. In addition the power thereof was varied in four types as follows; that is to say, "control" (with no irradiation of ultraviolet light) is indicated as 4A, at $0.5 \ mW/cm^2$ as 4B, $1.3 \ mW/cm^2$ as 4C and $3.0 \ mW/cm^2$ as 4D.

In the above experiment there is proved that the stronger the illumination power is, the greater the lowering of activity and at the illuminating power of more than $0.5 \ mW/cm^2$ of ultraviolet light, the activity declined to almost half after two hours of irradiation. Therefore there is proved that the limit of illuminating power of ultraviolet light with minimum lowering of enzymes to be $0.5 \ mW/cm^2$.

EXAMPLE 3

Then there was made a comparison between the effect of disinfection by using overhead irradiation disclosed in Example 2 and dipping irradiation of ultraviolet light at $0.5 \ mW/cm^2$, and the disinfection by using sodium hypochlorite. Though a sodium hypochlorite is inappropriate to disinfection of immobilized biocatalysts because a sodium hypochlorite disactivates immobilized biocatalysts, it is stronger in disinfecting power than the conventional surface active agent like quaternary ammonium salt, 10–50% of propylene glycol or the like so that it was adopted for this experiment. In addition in this experiment protease "S" was used as immobilized enzymes, #8, #9, #10 and #11 of "chitopearls" as carriers, and the said carriers were adopted after being contaminated by planting heat-resisting germs of Bacillus subti-lis NCOD 2130 in acid casein solution.

First, as a sodium hypochlorite solution 40 ml of solution of available chlorine concentration was prepared at 20 ppm to which extent the activity of enzymes would not be affected and 5 g.wet of the said immobilized enzymes are poured, and then the said immobilized enzymes are stirred for ten minutes, and resulted in as the following TABLE.

TABLE

| Carrier | (g · wet) Number of micobe before disinfection | Number of micobe After disinfection |
|---|---|---|
| #8 | $8.2 * 10^4$ | $4.5 * 10^4$ |
| #9 | $4.0 * 10^3$ | $1.2 * 10^4$ |
| #10 | $7.0 * 10^4$ | $5.1 * 10^4$ |
| #11 | $1.2 * 10^5$ | $1.0 * 10^4$ |

In this experiment, it resulted that the disinfection by sodium hypochlorite whatever carriers did not made any particular effect of disinfection.

Figure 5:
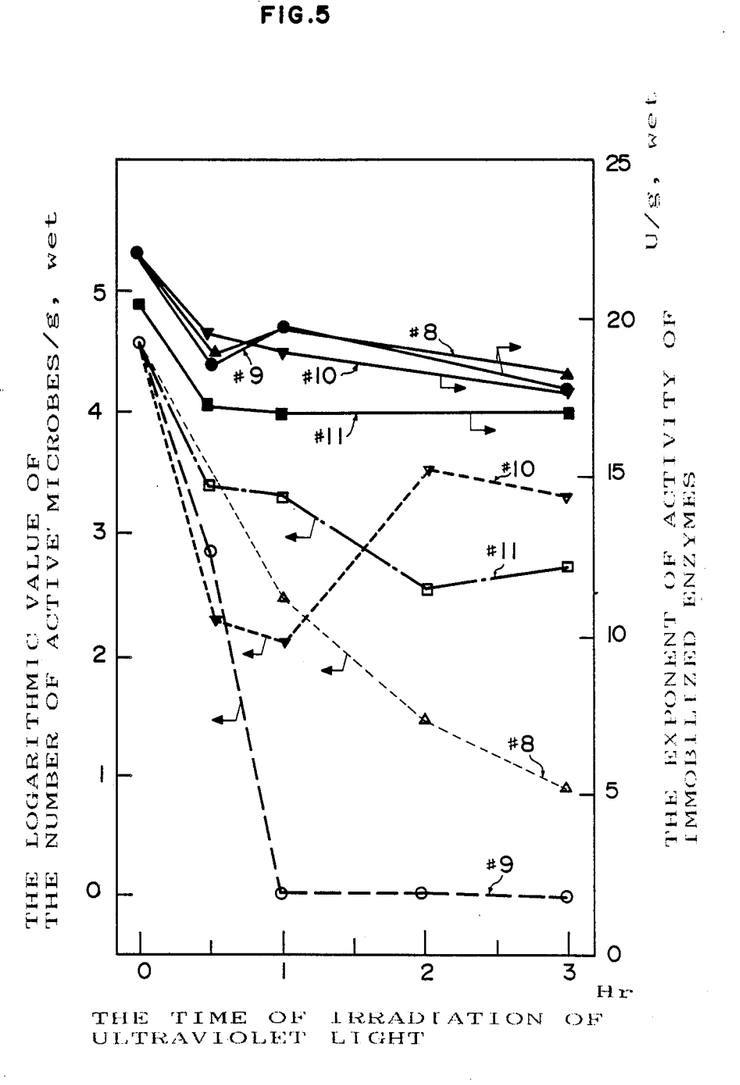

Then the result of the experiment of decreasing of the number of active microbes by using overhead irradiation and dipping irradiation of ultraviolet light at the illuminating power of 0.5 mW/cm$^2$ is shown as FIG. 5.

In addition dotted lines in FIG. 5 are indicated as the time of irradiation of ultraviolet light for the horizontal axis and as the logarithmic value of the number of active microbes of immobilized enzymes for the vertical axis, and solid lines are indicated as the time of irradiation of ultraviolet light for the horizontal axis and as the exponent of activity of immobilized enzymes for the vertical axis. And indications #8, #9, #10 and #11 are the numberings of goods of "chitopearl" used as carriers.

In this experiment both overhead irradiation and dipping irradiation of ultraviolet light resulted in giving effects of disinfection when whatever carriers were used, and after 30 minutes of irradiation logarithmic value of the number of active microbes of immobilized enzymes were decreased at 1-2 orders. Especially, "chitopearl" #9 gave a particular effect that the number of microbes were at zero after an hour of irradiation. Therefore it proved that the smoother the construction of surface of carrier becomes, the more effective the disinfection becomes.

Comparing to the this effect of disinfection, the exponent of activity of immobilized enzymes were not so changed when any of "chitopearls" #8, #9, #10 and #11 as carriers were used and therefore the activity of immobilized enzymes were not lost.

As above stated the disinfections of immobilized biocatalysts by using overhead irradiation and dipping irradiation of ultraviolet light besides at the ceiling limit of illuminating power of 0.5 mW/cm$^2$ give particular effect both in disinfection and in activity of enzymes.

Figure 1:
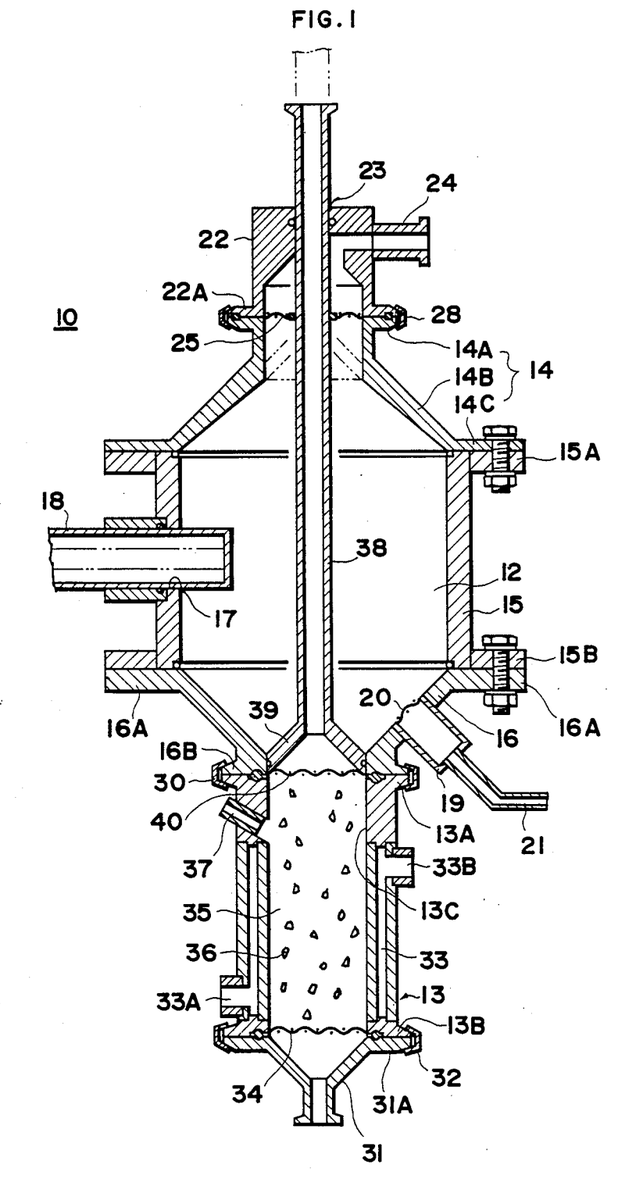
FIG. 1 is a sectional view which shows one embodiment of the reactor provided with fluidized chamber according to the present invention.
Figure 2:
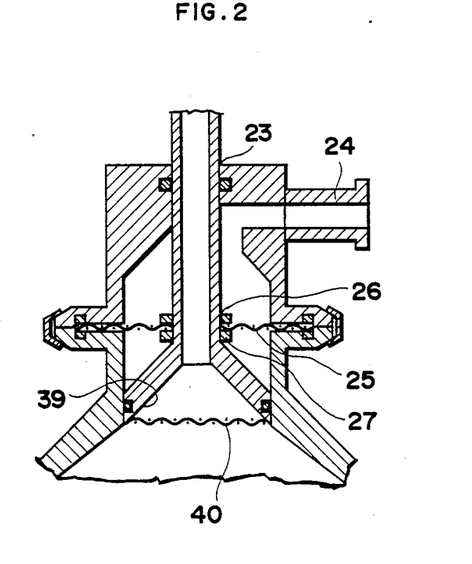
FIG. 2 is a detailed sectional view around the upper cylinder portion 22 in which the outside of the head opening 39 of inner tube 38 is connected with the bottom of the engagement 26 of FIG. 1, FIG. 3 through FIG. 5 are graphic charts showing the experimental examples in the method of disinfecting immobilized biocatalysts.

The apparatus according to the present invention will be explained with reference to the drawings hereinafter:

FIG. 1 and FIG. 2 are an example of embodiment. Reference numeral 10 shows a reactor wherein a hollow column chamber 13 is connected with a down portion of a hollow fluidized chamber 12. The fluidized chamber 12 is formed by a central cylinder portion 15, an upper funnel portion 14 and lower funnel portion 16. The lower flange 14C of the upper funnel portion 14 and the upper flange 15A of the cylinder portion 15, and the lower flange 15B of the cylinder portion 15 and upper flange 16A of the lower funnel portion 16 are bolted together respectively.

A washing gateway 19 e.g. a valve, valved tube or the like passes into fluidized chamber 12 at the down portion of the lower funnel portion 16, and the washing gateway 19 is provided a filter 20 at about the same level as the surface of the wall of the lower funnel portion 16, and the other end of the washing gateway 19 is connected with a tube 21. Further the washing gateway 19 is usually used for the exit of washing fluid but the usage as an entrance is also available.

The upper funnel portion 14 is constructed as a connection from the upper level with the upper flange 14A, funnel 14B and the lower flange 14C respectively. At the upper flange 14A of the upper funnel portion 14, the lower flange 22A of the upper portion of the fluidized chamber 12, shown as a cylinder portion 22, is connected through clamp coupling 28. In the upper cylinder portion 22 there is provided a through hole 23 for the inner tube 38 at the top surface and the washing gateway 24 at the top end. Between the upper flange 14A and the lower flange 22A of the upper cylinder portion 22 there is disposed a solids outflow-preventing net or screen 25 and at the center of the said net or screen there is provided an engaging hole 26 and O-ring 27 engageable with the inner tube 38. Further, washing gateway 24 is usually used for the exit of washing liquid but the usage as an entrance is also available.

On the other hand, at the lower portion of the lower funnel portion 16 there is provided a flange 16B which is connected with the upper flange 13A of the column chamber 13 through a clamp coupling 30. And the lower flange 13B of the column chamber 13 is connected with the upper flange 31A of the funnel tube 31 through a clamp coupling 32. Around the perimeter of the column chamber 13 there is provided a jacket 33, and 33A and 33B are an entrance and exit respectively for the cooling water filled up in the jacket 33.

Reference numeral 38 shows an inner tube which is disposed through the hole 23 of the upper cylinder portion 22 and the engaging hole 26 of the outflow-preventing net or screen 25, and at an end of the inner tube there is provided extendingly a funnel head opening 39, and at the outer surface of the head opening 39 there is capped a solids outflow-preventing net or screen 40. The end of the perimeter of the head opening 39 is contactable with a juncture between column chamber 13 and fluidized chamber 12, e.g. contactable with an inner wall 13C of the column chamber 13. Further, the inner tube 38 is available for vertical movement and when the washing and disinfecting of immobilized biocatalysts are desired, such may be achieved when the inner tube 38 is raised so that the outside (upper side) of the head opening 39 is contacted with the upper inside of the upper flange 14A of the upper funnel portion 14.

At the bottom of the column chamber 13 there is provided a solids outflow-preventing net or screen 34 and immobilized biocatalysts 36 are filled up in the filling chamber 35 of the coloumn chamber 13, surrounded by a solids outflow-preventing net or screen 40, an inner wall 13C and a lower solids outflow-preventing net or screen 34. Reference numeral 37 is a pick-up gate of samples of immobilized biocatalysts and through the said pick-up gate immobilized biocatalysts are picked up at will and therefore available for investigating the condition of the washing, the disinfecting and the potential of elution of the said immobilized biocatalysts.

On the other hand, at the trunk of the central cylinder portion 15 of the fluidized chamber 12, there are through openings for the ultraviolet light source and through ultraviolet light source opening 17 ultraviolet light lamp 18 is available for insertion into the inside of the central cylinder portion 15. When the inner tube 38 is dropped and contacted with the juncture, e.g. the wall 13C of the column chamber 13, the use of ultraviolet lamp is available when the ultraviolet lamp is constructed so as not to prevent the movement of the inner tube 38 in the fluidized chamber.

The example of the elution, washing and disinfecting of immobilized biocatalysts will illustrate the working of the reactor provided with the fluidized chamber as shown in FIG. 1. The reactive solution, e.g. with matrix, is passed from the solution gate of the inner tube 38 and then goes to the filling chamber 35 through the solids outflow-preventing net or screen 40, and is reacted by immobilized biocatalysts. In this case the head opening 39 is contacted with the juncture, e.g. inner wall 13C of the column chamber 13. And hereinafter the reacted solution passes through the lower solids outflow-preventing net or screen 34 and is transferred to the next process.

Further, during this reaction the washing of the inside of the fluidized chamber 12 is available, when the washing liquid is introduced at a high pressure from the washing gateway 24. Thus, the washing of the inside of the fluidized chamber 12 is available separately from the washing of the immobilized biocatalysts. As for the washing of the inside of the fluidized chamber 12, it is available when the washing liquid is introduced from the washing gateway 24 and exhausted from the gateway 19.

When desiring the washing and the disinfecting of the immobilized biocatalysts because of loss of pressure due to adhesion of protein or the like, the inner tube 38 is raised up and the top end of the outside of the head opening 39 is contacted with the bottom of the engaging hole 26 of the upper solids outflow-preventing net or screen 25, which is shown in FIG. 2.

Then the washing liquid is introduced through the funnel tube 31. In this process immobilized biocatalysts are floated in the fluidized chamber 12. Before the washed immobilized biocatalysts are returned into the column chamber 13, the inner tube 38 is dropped and contacted with the juncture, e.g. inner wall 13C of the column chamber 13. Through the said operation in the fluidized chamber 12, there occurs a scroll or vortex of the washing liquid in the fluidized chamber 12 when the washing liquid is introduced from the washing gateway 24, and the immobilized biocatalysts are stirred and washed by the said scroll of the washing liquid. Then the washing liquid is exhausted through the washing gateway 19. In this case, different from the conventional art, the washing without disactivating immobilized biocatalysts is available because the washing of only the immobilized biocatalysts in the fluidized chamber 12 is performed. And after the said washing, ultraviolet lamp 18 is inserted from the ultraviolet opening 17 into the inside of the central cylinder portion 15 and then the disinfection of the immobilized biocatalysts is performed.

While the washing and the disinfecting of immobilized biocatalysts are operated in the fluidized chamber 12, in the column chamber 13 the washing of the inside of the column chamber is available separately by introducing the washing liquid by using funnel tube 31 and by exhausting the washing liquid to the top of the inner tube 38 from the funnel head opening 39 to the inner tube 38.

After washing of the inside of the column chamber 13 is made, the washing liquid is exhausted. Then the inner tube 38 is raised again and the top end of the outside of the head opening 39 is contacted with the bottom of the engaging hole 26 of the upper solids outflow-preventing net or screen 25. In this process the washing and the disinfecting is completed and the immobilized biocatalysts floating in the fluidized chamber 12 are settled into the column chamber 13. And then the end of the perimeter of the head opening 39 of the inner tube 38 is contacted with the inner wall 13C of the column chamber 13. And then the remained liquid in the fluidized chamber 12 is exhausted outside from the washing gateway 19 through the filter or screen 20.

While the invention has been particularly shown and described with reference to preferred embodiment thereof, it will be understood by those skilled in the art that the foregoing and other changes in form and details can be made therein without departing from the spirit and scope of the invention.

What is claimed is:

1. A reactor for containing a bed of reactive solids and provided with a fluidized chamber for periodic treatment of the reactive solids, comprising:
   (1) a generally vertically-disposed column chamber for containing the reactive solids;
   (2) a first screen disposed near a lower end of the column chamber for supporting and containing the reactive solids;
   (3) a fluidized chamber of greater volume than said column chamber and being disposed generally above and in fluid communication with said column chamber at a fluid communication juncture therebetween;
   (4) a straight hollow interior inner tube extending from an upper portion of the fluidized chamber to near said juncture and terminating in a head portion, and wherein the head portion is contactable with the juncture to fluidly seal the column chamber from the fluidized chamber;
   (5) a head opening in said head portion in fluid communication with the hollow interior of said inner tube;
   (6) a second screen disposed over said head opening so that the reactive solids are containable in said column chamber between vertical inner walls of the column chamber and said first and second screens;
   (7) means for allowing movement of said inner tube vertically upwardly until said head portion is contactable with an inner wall of the upper portion of said fluidized chamber at a contact point, so as to fluidly seal the upper portion of the fluidized chamber from a lower portion of the fluidized chamber;
   (8) a first fluid gateway disposed in said fluidized chamber and in a portion thereof above said contact point;
   (9) a third screen disposed between said contact point and said first fluid gateway;
   (10) means for introducing a washing fluid or the like into a bottom portion of the column chamber such as to move the reactive solids disposed therein from said column chamber and fluidize the solids in the fluidized chamber; and wherein said fluidized chamber has a configuration such that when said washing fluid is discontinued, the reactive solids settle into said column chamber and are again retainable therein by movement of said head portion to said juncture; and
   (11) means for introducing a washing liquid through the first gateway and passing the washing liquid out of a second gateway disposed in said fluidized chamber and having a screen thereon when said head portion is disposed at said juncture;

whereby, the reactive solids may be washed in said fluidized chamber while the column chamber is being simultaneously washed with separate wash water or the fluidized chamber may be washed while reactive solids in the column chamber are reacting with a reactable solution.

2. A reactor provided with fluidized chamber according to claim 1, wherein the second fluid gateway is disposed near said juncture.

3. A reactor provided with a fluidized chamber according to claim 1, wherein an ultraviolet light source is disposable in the fluidized chamber for disinfecting the reactive solids while the reactive solids are disposed in the fluidized chamber during washing of the reactive solids.

* * * * *